(12) United States Patent
Petyaev

(10) Patent No.: US 10,849,336 B2
(45) Date of Patent: Dec. 1, 2020

(54) COCOA-BASED FOOD PRODUCTS

(71) Applicant: IP Science Limited, Cambridge (GB)

(72) Inventor: Ivan Petyaev, Cambridge (GB)

(73) Assignee: IP SCIENCE LIMITED, Cambridge (GB)

( * ) Notice: Subject to any disclaimer, the term of this patent is extended or adjusted under 35 U.S.C. 154(b) by 0 days.

(21) Appl. No.: 14/361,795

(22) PCT Filed: Nov. 30, 2012

(86) PCT No.: PCT/GB2012/052973
§ 371 (c)(1),
(2) Date: May 30, 2014

(87) PCT Pub. No.: WO2013/079967
PCT Pub. Date: Jun. 6, 2013

(65) Prior Publication Data
US 2014/0288187 A1  Sep. 25, 2014

(30) Foreign Application Priority Data

Dec. 2, 2011 (GB) .................................. 1120772.7

(51) Int. Cl.
| A23G 1/42 | (2006.01) |
| A23G 1/32 | (2006.01) |
| A61K 36/185 | (2006.01) |
| A61K 31/01 | (2006.01) |
| A23L 33/155 | (2016.01) |
| A23L 33/00 | (2016.01) |
| A23L 33/105 | (2016.01) |

(52) U.S. Cl.
CPC .............. *A23G 1/42* (2013.01); *A23G 1/32* (2013.01); *A23G 1/426* (2013.01); *A23L 33/105* (2016.08); *A23L 33/155* (2016.08); *A23L 33/30* (2016.08); *A61K 31/01* (2013.01); *A61K 36/185* (2013.01); *A23V 2250/213* (2013.01)

(58) Field of Classification Search
CPC .................................. A23G 1/30; A23G 1/42
See application file for complete search history.

(56) References Cited

U.S. PATENT DOCUMENTS

| 4,206,245 | A | 6/1980 | Drevici et al. | |
| 4,307,126 | A | 12/1981 | Sano et al. | |
| 5,705,526 | A * | 1/1998 | Fujiwara ................. | A61K 31/01 514/458 |
| 6,262,109 | B1 * | 7/2001 | Clark ....................... | A61K 31/01 514/458 |
| 8,586,107 | B2 | 11/2013 | Garnier et al. | |
| 2006/0134294 | A1 | 6/2006 | McKee et al. | |
| 2007/0269493 | A1 | 11/2007 | Lang | |
| 2010/0143543 | A1 * | 6/2010 | Hitz ........................ | A23G 1/426 426/73 |

FOREIGN PATENT DOCUMENTS

| AU | 2012/343524 B2 | 9/2018 |
| FR | 2471144 A1 | 6/1981 |
| FR | 2882895 A1 | 11/2005 |
| JP | H09-002947 | 6/1995 |
| JP | 2008125382 A | 6/2008 |
| JP | 2009/179622 A | 8/2009 |
| JP | 2010/538674 A | 12/2010 |
| KR | 102006-0132688 | 12/2006 |
| WO | WO2005075575 A1 | 8/2005 |
| WO | WO2009/037562 | 3/2009 |
| WO | WO 2009/084275 | 7/2009 |
| WO | WO2011012612 A2 | 3/2011 |
| WO | WO2011/107259 | 9/2011 |

OTHER PUBLICATIONS

Ried et al., Maturitas, 2011, vol. 68, pp. 299-310.*
Story et al., Annu. Rev. Food Sci. Technol., 2010, vol. 1, pp. 189-210 (Year: 2010).*
K. Ried et al., "Dark chocolate or tomato extract for prehypertension: a randomised controlled trial" BMC Complementary and Alternative Medicine, Jul. 2009, pp. 1-13.
Souci et al., "Food compositions and nutrition table", 2000, XP002695915, p. 1116.
Bose, KSC, PHD, Effect of lycopene from cooked tomatoes on serum antioxidant enzymes, lipid peroxidation rate and lipid profile in coronary heart disease, Singapore Med J 2007; 48 (5) : pp. 415-420.
Thies F. et al., Effect of a tomato-rich diet on markers of cardiovascular disease risk in moderately overweight, disease-free, middle-aged adults: a randomized controlled trial, Am J Clin Nutr 2012; 95:1013-22, USA, 2012 American Society for Nutrition, pp. 1013-1022.
Subhash K. et al., Effect of Lycopene from Tomatoes (Cooked) on Plasma Antioxidant Enzymes, Lipid Peroxidation Rate and Lipid Profile in Grade-I Hypertension, Annals of Nutrition & Metabolism, 2007;51: pp. 477-481, Nov. 20, 2007.
Collins JK et al., Lycopene from two food sources does not affect antioxidant or cholesterol status of middle-aged adults, Nutritional Journal, 2004, 3:15, pp. 1-7, Sep. 15, 2004.
Zheng et al., Flavanoid Compounds and the Pharmacological Activity thereof, Int'l Met Bot. Drug Fascicle, vol. 20, No. 2, pp. 58-61, Dec. 31, 2015.
Chen et al., Studies and development of lycopene, vol. 41, No. 6, pp. 589-593. Guangxi Ag. Sci., Dec. 31, 2010.

(Continued)

*Primary Examiner* — James D. Anderson
(74) *Attorney, Agent, or Firm* — Greer, Burns & Crain, Ltd.

(57) ABSTRACT

The invention is concerned with food products comprising one or more cocoa bean products and a carotenoid compound, particularly with food products which are, or comprise, chocolate. The products of the invention may be used in reducing elevated total cholesterol, triglycerides and inflammatory damage, as well as improving tissue microcirculation and tissue oxygenation.

6 Claims, No Drawings

(56) References Cited

OTHER PUBLICATIONS

Baba et al., "Plasma LDL and HDL Cholesterol and Oxidized LDL Concentrations Are Altered in Normo- and Hypercholesterolemic Humans and Intake of Different Levels of Cocoa Powder1", The Journal of Nutrition and Disease, Apr. 5, 2007, pp. 1436-1441.
Engler, PhD, et al., "The Emerging Role of Flavonoid-Rich Cocoa and Chocolate in Cardiovascular Health and Disease", Nutrition Reviews, vol. 64, No. 3, Mar. 2006, pp. 109-118.
Tokede, et al., "Effects of Cocoa Products/Dark Chocolate on Serum Lipids: a Meta-analysis", European Journal of clinical Nutrition (2011) 65, 879-886, 2011 Macmillian Publishers Limited.
Lee, et al., "Astaxanthin inhibits nitric oxide production and inflammatory gene expression by suppressing 1(kappa)B kinase-dependent NF-kappaB activation", Mol Cells, Aug. 31, 2003, 16(1):97-105.
Tang Xiangyu et al.,"A study of the effect and mechanism of lycopene on oxidative damage in rabbit hyperlipid vessels", Chinese Clinical Pharmacology and Therapeutics, 2006, 11(2), pp. 158 to 161.
Yu Wenli et al., "Experimental Evaluations on Physiological Function of Lycopene", Journal of Wuxi University of Light Industry, 1st Edition, col. 24, pp. 99 to 101 and disclosed in 2005.
Chen Weiqiang "Plasma LDLand HDL cholesterol and oxidized LDL concentrations are altered in normo- and hypercholesterolemic humans after intake of different levels of cocoa powder", Nutrition Newsletter, 2nd Edition, pp. 38-39, Dec. 31, 2007.
Kardinaal et al., "Antioxidants in adipose tissue and risk myocardial infarction: The EURAMIC study", The Lancet, Dec. 4, 1993, pp. 1379-1384, vol. 342.
Fraga et al., "Regular consumption of a flavanol-rich chocolate can improve oxidant stress in young soccer players", Clinical & Developmental Immunology, Mar. 2005, pp. 11-17, vol. 12(1).
Grassi et al., "Cocoa Reduces Blood Pressure and Insulin Resistance and Improves Endothelium-Dependent Vasodilation in Hypertensives", Hypertension, Aug. 2005, pp. 398-405, vol. 46.
Wang et al., "A Dose-Response Effect from Chocolate Consumption on Plasma Epicatechin and Oxidative Damage 1,2", Chocolate: Modern Science Investigates an Ancient Medicine, American Society for Nutritional Sciences, 2000, pp. 2115S-2119S, vol. 130.
Almoosawi et al., The effect of polyphenol-rich dark chocolate on fasting capillary whole blood glucose, total cholesterol, blood pressure and glucocorticoids in healthy overweight and obese subjects, British Journal of Nutrition, 2010, pp. 842-850, vol. 103.
Muniyappa et al., "Cocoa consumption for 2 wk enhances insulin-mediated vasodilatation without improving blood pressure or insulin resistance in essential hypertension 1,2,3", National Institute of Health, American Journal of Clinical Nutrition, Dec. 2008, pp. 1685-1696, vol. 88(6).
Crews et al., "A double-blind, placebo-controlled, randomized trial of the effects of dark chocolate and cocoa on variables associated with neuropsychological functioning and cardiovascular health: clinical findings from a sample of iealthy, cognitively intact older adults", American Journal of Clinical Nutrition, Apr. 2008, pp. 2 pages, vol. 87 (4):872-80).
Wan, et al., "Effects of cocoa powder and dark chocolate on LDL oxidative susceptibility and prostaglandin concentrations in humans", American Journal of Clinical Nutrition, Nov. 2001, 2 pages, vol. 74(5):596-602.
Gorusupudi et al., "Wheat germ oil: a potential facilitator to improve lutein bioavailability in mice", Nutrition, May 29, 1 page, 2013, (5):790-5. doi: 10.1016/j.nut.2012.11.003. Epub Jan. 22, 2013.
Arshad et al., "Wheat germ oil and α-lipoic acid predominantly improve the lipid profile of broiler meat", J. Agric Food Chem., Nov. 20, 2013, 1 page, 61(46):11158-65. doi: 10.1021/jf4041029. Epub Nov. 5, 2013.
Lee, et al., "Astaxanthin Inhibits Nitric Oxide Production and Inflammatory Gene Expression by Suppressing IkB Kinase-dependent NF-KB Activation", Molecules and Cells, Aug. 31, 2003, pp. 97-105, vol. 16, No. 1.
Keen, et al. "Cocoa antioxidants and cardiovascular health", Am J. Clin. Nutr. 2005, pp. 298S-303S, vol. 81.
Mccance & Widdowson's, "Sugar, preserves and snacks", Institute of Food Research, 1992, pp. 1-2.
Agarwal, et al., "Tomato Lycopene and Low Density Lipoprotein Oxidation: A Human Dietary Intervention Study", Lipids, 1998, pp. 981-984, vol. 33, No. 10.
Jia et al., "Short-term effect of cocoa product consumption on lipid profile: a meta-analysis of randomized contgrolled trials", Am J. Clin, Nutr, 2010, pp. 218-225, vol. 92.
Meng, et al., "Phenolic and Theomromine Contents of Commercial Dark, Milk and White Chocolates on the Malaysian Market", Molecules, 2009, pp. 200-209, vol. 14.
Taubert et al., "Effects of Low Habitual Cocoa Intake on Blood Pressure and Bioactive Nitric OxideA Randomized controlled Trial", JAMA, 2007, pp. 49-60, vol. 298, No. 1.
Bose et al., "Effect of lycopene from cooked tomatoes on serum antioxidant enzymes, lipid peroxidation rate and lipid profile in coronary heart disease", Singapore Med J., 2007, pp. 1-6, vol. 48, No. 5.
Upritchard et al., "Effects of Supplementation With Tomato Juice, Vitamin E, and Vitamin Con LDL Oxidation and Products of Inflammatory Activity in Type 2 Diabetes", Diabetes Care, Jun., 2000, pp. 733-738, vol. 21 No. 6.
Richelle, et al., "Human Nutrition and Metabolism", American Society for Nutritional Sciences, Sep. 2001, pp. 4040-408.
Souci et al., Milk Chocolate, Food Composition and Nutrition Tables, 2000, pp. 1116.

* cited by examiner

COCOA-BASED FOOD PRODUCTS

CROSS-REFERENCES TO RELATED APPLICATIONS

This patent application is a national stage of PCT/GB2012/052973 which was filed Nov. 30, 2012 and claims its priority to United Kingdom Patent Application 1120772.7 which was filed Dec. 2 2011, the entire disclosures of both applications are incorporated herein by reference.

FIELD OF THE INVENTION

This invention relates to cocoa-based food products, such as chocolate, which have beneficial effects on parameters of metabolism in individuals including levels of triglycerides, cholesterol and other lipids, molecular oxygen transport and its metabolism, oxygen tissue saturation and microcirculation, control of hypoxia/ischaemia, as well as markers of inflammation and inflammatory oxidative damage.

BACKGROUND TO THE INVENTION

Food products based on cocoa beans, such as chocolate and other products containing cocoa solids, cocoa butter, cocoa liquor, and/or their derivatives, are widespread in the Western society. Although these cocoa-based products often contain flavonols and flavonoids, which have been associated with certain health benefits, they also contain high levels of cocoa butter or other high-fat ingredients. This high fat content means that cocoa-based food products are one of the dietary factors responsible for the growth of Metabolic Syndrome, Diabetes II and Obesity in the modern society.

Cocoa-based food products, such as chocolate, have been associated with health benefits, such as improvements in endothelial vascular function, including positive effects on blood pressure, and with antioxidant and anti-inflammatory properties [Keen et al *Am J Clin. Nutr.* 2005, 81(suppl): 298S-303S].

However, the effects of chocolate on blood lipid concentrations are either inconclusive or negative. Consumption of 105 g of dark chocolate has been reported to result in a mild reduction of total blood lipid concentrations of 11% [Cesar et al *Clinical & Developmental Immunology*, 2005; 12(1) 11-17], but this trial was done on an exceptional group of young elite sportsmen and positive blood lipid changes may be attributed to the overall improvement of their physical performance.

Meta-analysis of eight clinical trials on dark chocolate or cocoa powder showed an observed reduction in the cholesterol levels of up to 5.82 mg/dL, which was statistically insignificant [Lei et al *Am J Nutr* 2010; 92; 218-25]. Furthermore, the amount of the daily administered doses of cocoa phenols in these trials was equivalent of consumption of 100 g or more of the dark chocolate [Cheng et al *Molecules* 2009, 14: 200-209]. In other studies, when dark chocolate was consumed from 30 to 100 g daily, no changes were observed in the blood lipids [Taubert et al *JAMA*. 2007; 4, 298(1):49-60, Grassi et al Hypertension. 2005; 46(2):398-405].

The level of triglycerides in all the above studies above either had insignificant trends or did not change at all.

There are no reports of any health benefit, including on blood lipids, arising from consumption of the most common forms of chocolate, including milk chocolate and white chocolate.

Lycopene is known to be as a potent antioxidant. Its mild cholesterol-lowering effect has been reported from 13 clinical studies and was 7.55+6.15 mg/dL [Ried et: al Maturitas. 2011, 68(4):299-310]. However this effect was only observed for daily doses 25 mg of lycopene or above. There were no reports on the effect of lycopene on elevated triglycerides in human.

Although 25 mg of lycopene and above is considered to be safe for certain periods of administration, it is far above the daily level which could be consumed with a diet rich with tomato or tomato processed products (about 6-10 mg). Daily consumption of 6-10 mg lycopene has been reported to have no effect on cholesterol or other blood lipids [Bose et al Singapore Med J 2007; 48 (5); 415-420; Upritchard et al Diabetes Care, 2000, 236: 733-735].

SUMMARY OF THE INVENTION

The present invention is based on the unexpected finding that the combination of a carotenoid and a cocoa bean product can be used to reduced elevated cholesterol, reduce elevated triglyceride levels, reduce inflammatory oxidative damage and improve tissue microcirculation and oxygen transport. Given the high fat and sugar content of chocolate, such a finding was highly unexpected and indeed counter-intuitive.

Accordingly, the invention provides a food product comprising one or more cocoa bean products and a carotenoid compound.

The invention also provides such a food and/or beverage and/or nutraceutical product for use in:
(a) reducing levels of elevated cholesterol, LDL and/or triglyceride in an individual, preferably where the individual has elevated levels of cholesterol, LDL and/or triglyceride;
(b) reducing subclinical or clinical inflammation; reducing anti-inflammatory oxidative damage; increasing plasma molecular oxygen transport, microcirculation and tissue oxygen saturation, reducing already developed liver (micro-) damage and liver steatosis, liver and other organs, including peripheral, tissue hypoxia or ischaemia, increasing antioxidant activity and/or reducing or delaying symptoms of ageing in an individual;
(c) reducing postprandial cholesterol- and triglyceride-aemias, reducing size of chylomicrons and increasing rate of their clearance, reducing postprandial inflammatory and oxidative stress, reducing postprandial or other liver (micro-) damage and liver steatosis, liver and other organs, including peripheral tissue hypoxia or ischaemia, or delaying of above mentioned symptoms of fat, or excessive, or imbalance food intake in an individual;
(d) increasing oxygen transport in a subject, preferably where the subject has a respiratory disorder and/or lung damage; and/or strenuous physical or mental performance; and/or muscle wasting conditions; and/or
(e) slimming, weight reduction or dieting.

The invention additionally provides a method of:
(a) improving the appearance and performance of an individual comprising administering a nutracosmetic formulation or food or beverage product of the invention to the individual; and/or
(b) reducing or delaying signs of aging in an individual, preferably visible signs of aging, comprising administering a food product of the invention to the individual.

óThe invention also provides a method of:
The invention also provides a method of:
(a) reducing levels of elevated cholesterol, LDL and/or triglyceride in the blood of an individual comprising administering a food product of the invention to an individual in need thereof;
(b) reducing subclinical or clinical inflammation; reducing anti-inflammatory oxidative damage; increasing plasma molecular oxygen transport, microcirculation and tissue oxygen saturation, reducing already developed liver (micro-) damage and liver steatosis, liver and other organs, including peripheral, tissue hypoxia or ischaemia; increasing antioxidant activity and/or reducing or delaying symptoms of ageing in an individual; comprising administering a food product of the invention to an individual in need thereof;
(c) reducing postprandial cholesterol- and triglyceride-aemias, reducing size of chylomicrons and increasing rate of their clearance, reducing postprandial inflammatory and oxidative stress, reducing postprandial or other liver (micro-) damage and liver steatosis, liver and other organs, including peripheral tissue hypoxia or ischaemia, or delaying of above mentioned symptoms of fat, or excessive, or imbalance food intake in an individual; comprising administering a food product of the invention to an individual in need thereof;
(d) providing nutrition to an individual comprising administering a food product of the invention to an individual in need thereof; and/or strenuous physical or mental performance; and/or muscle wasting conditions; and/or
(e) slimming, weight reduction or dieting comprising administering a food product of the invention.

The invention also provides a chocolate bar and/or chocolate beverage comprising a carotenoid, preferably where the carotenoid is a lycopene compound.

DETAILED DESCRIPTION THE INVENTION

This invention relates to the unexpected finding that incorporating carotenoid compounds into food products which contain cocoa-bean based products, such as cocoa solids, cocoa butter, cocoa liquor, and/or their derivatives, causes these food products to exert a positive effect on levels of triglycerides, cholesterol, LDL, and other metabolic parameters in individuals, despite being rich in saturated and unsaturated fats. Given the high fat content of food products such as chocolate, the finding that the combination of a carotenoid and chocolate is able to reduce those parameters was unexpected and counter-intuitive.

An aspect of the invention provides a food product which comprises one or more cocoa-bean products and a carotenoid compound. Typically, the carotenoid compound is an isolated carotenoid compound.

The food product may comprise a homogenous matrix which contains the cocoa-bean products and the carotenoid compound. For example, the cocoa-bean products and carotenoid compound may be blended together in a chocolate or cocoa-butter matrix.

A cocoa bean product is an extract, fraction or isolate from cocoa beans (i.e. beans of the cacao tree (*Theobroma cacao*)). Suitable cocoa bean products are well-known in the art and include cocoa solid, cocoa liquor and/or cocoa butter. For example, a food product may comprise one or more of cocoa solid, cocoa liquor and/or cocoa butter.

In some instances cocoa nibs or fragments thereof, chocolate liquor, partially and fully-defatted cocoa solids (e.g. cocoa powder), cocoa extract or a fraction thereof may be employed.

Cocoa solid (also known as cocoa powder) is a low-fat extract of cocoa beans, which contains flavanols, flavanoids, caffeine and theobromine. Cocoa solid may be produced by removing the fat component (cocoa butter) from the cocoa bean and grinding the remaining material, excluding the shell, to a powder using techniques which are well-known in the art, such as Broma processing. In some embodiments, cocoa powder may be treated with an alkaline substance such as potassium carbonate to reduce acidity and darken the colour (Dutch processing).

Cocoa butter is a high-fat extract of cocoa beans which is high in stearic acid, palmitic acid and other saturated fats. Cocoa butter may be produced from whole or ground cocoa beans using techniques which are well-known in the art.

Cocoa liquor is a cocoa bean extract which contains both cocoa solid and cocoa butter. Cocoa liquor may be produced by grinding and melting the cocoa bean nib (centre) to a smooth liquid state in accordance with techniques which are well-known in the art. Chocolate liquor does not contain non-cocoa vegetable fat and may also be referred to as "chocolate", "unsweetened chocolate", "baking chocolate", or "bitter chocolate".

In other embodiments, cocoa bean products may include derivatives or fermentation products of cocoa bean extracts, isolates or fractions.

Preferably, the food product comprises cocoa butter; cocoa solid; or both cocoa butter and cocoa solid.

For example the food product may contain at least 1% by weight, at least 10% by weight, at least 15% by weight, at least 20% by weight, at least 25% by weight or at least 30%, or at least 40% by weight cocoa butter. The food product may contain an amount of cocoa butter in a range comprising any of the above two values as endpoints.

In some embodiments, a food product may further comprise non-cocoa fats, such as vegetable or animal fats in addition to cocoa butter.

In some embodiments, a food product may be devoid of cocoa butter. For example, a food product may contain animal or non-cocoa vegetable fat instead of cocoa butter. Non-cocoa vegetable fats may include vegetable oils. Suitable vegetable oils, such as palm oil, soybean oil rapeseed oil and olive oil, are well known in the art.

The total fat content of a food product described herein may be at least 10% by dry weight, at least 15% by dry weight, at least 20% by dry weight, at least 25% by dry weight, at least 30% by dry weight or at least 35% by dry weight or at least 40% by dry weight. The fat content may be, for instance, in a range comprising any two such values as endpoints.

Additionally or alternatively, the food product may contain at least 5% by weight, at least 15% by weight, at least 20% by weight, at least 25% by weight, at least 30% by dry weight or at least 35% by weight, or at least 40% by weight dry cocoa solid. In some instances, the amount of cocoa solid may be at least 50% by weight, at least 60% by weight, at least 75% by weight, at least 80% by weight, at least 85% by weight, at least 90% by weight or even at least 95% by weight dry cocoa solid, particularly when the food stuff is a dark chocolate. The amount of weight of dry cocoa solid may be, for instance, in the range comprising any two of those values as endpoints.

In some embodiments, a food product may be devoid of cocoa solid.

For the avoidance of doubt, aspects of the invention provide food products which comprise all combinations of the above parameters of cocoa solid, cocoa butter and total fat.

In some embodiments, the cocoa bean products may form a chocolate matrix. The carotenoid compound may be incorporated into the chocolate matrix by blending or admixing.

Any cocoa-based food product may be supplemented with a carotenoid compound as described herein. For example, the food product may be a foodstuff, a beverage or a dietary supplement or nutraceutical product.

Foodstuff products include bread, flour, cereal, biscuit, pastry, dairy products, such as cheese spread, cheese, cream and yoghurt, fillings, pastes, sauces and mousses. Other suitable foodstuffs are well known in the art.

In some preferred embodiments, foodstuff products may include confectionery products, such as chocolate. Especially preferred embodiments of the invention provide chocolate comprising a carotenoid compound, as described herein.

Chocolate may include dark chocolate, milk chocolate, or white chocolate.

In one preferred instance, the foodstuff of the invention may be a chocolate bar, for instance a dark, plain or milk chocolate bar comprising a carotenoid, such as any of those discussed herein. The amount of carotenoid in the bar may be, for instance, any of the amounts of carotenoid specified herein.

Dark chocolate, milk chocolate and white chocolate are subject to defined identity standards (for example, by the Food and Drug Administration (USA), EU and Food Standards Agency (UK); see for example EU directive 2000/36/EC; FDA 21 CFR Part 163 Federal Register: 2002 67 193 62171-62178). In one instance, a composition of the invention may be a standard of identity (SOI) chocolate, in others it is a non-SOI chocolate.

The ingredients of dark chocolate, milk chocolate, white chocolate or other forms of chocolate are well-known in the art. For example, dark chocolate typically comprises sugar, cocoa butter (e.g. at least 12% by weight), cocoa solids (e.g. at least 35% by weight), and optionally vanilla. Fat content may vary but averages between 30%-35%. Dark chocolate is sometimes referred to as sweet or semisweet chocolate. Milk chocolate may comprise sugar, cocoa butter, cocoa solids, vanilla or other flavourings, and milk, milk powder or cream. Milk chocolate typically contains at least 20% cocoa solid and at least 12% milk solids by weight. White chocolate may comprise sugar, cocoa butter, milk or milk powder, and vanilla and lacks cocoa solids. White chocolate typically contains at least 20% cocoa butter, 14% total milk solids, and less than 55% sugar.

In one instance, the food product of the invention may be about 100 g, 150 g, 200 g, 250 g, 300 g, 400 g or 500 g in weight or may have a weight in a range with any two of those values as endpoints. In a preferred instance, the foodstuff may be a chocolate bar of such weight.

The foodstuff may be a candy bar, for instance a chocolate coated candy bar. The foodstuff may take the form of individual chocolates, bagged chocolates or a box of chocolates. The chocolate may be in a formed shape. In one instance the foodstuff is an Easter egg. The invention may be provided in the form of chocolate icing or a cake comprising a carotenoid and chocolate. The invention also provides fruit or nuts coated with a chocolate of the invention. The invention also provides sweets or candy coated with a chocolate of the invention.

The invention also provides a chocolate of the invention provided in the form of a single serving dose, for instance in 10 to 30 g amounts, as well as a packet of such single serving doses. The invention also provides a chocolate bar of the invention segmented, for instance segmented so that it can be broken into single serving dosages.

The foodstuff of the invention may be, in other instances, a cake, cheesecake, baked snack, brownie, cookie or biscuit, a meal replacement bar, a rice cake, ice cream or other pudding or dessert. In some instances, the invention provides such products coated in, or comprising, a chocolate of the invention. The products may for instance comprise the chocolate in the form of chips or in a central region.

Beverages may include any drink which comprises cocoa-bean products and may include cocoa, drinking chocolate, milk shakes, and other dairy and non-dairy drinks. Beverages may be non-alcoholic or alcoholic. The formulation of suitable beverages is well-known in the art. In one preferred instance, the beverage is a chocolate milkshake. In another instance, a powder, gel or cube for making up as a beverage is also provided. The invention also provides a hot chocolate, chocolate or cocoa drink, as well as a chocolate/cocoa shot drink comprising a product of the invention.

Dietary supplements or nutraceutical products may be in any form suitable for oral administration (e.g., by ingestion) and may be presented as discrete units such as capsules, cachets or tablets; as a powder or granules; as a solution or suspension in an aqueous or non-aqueous liquid; or as an oil-in-water liquid emulsion or a water-in-oil liquid emulsion; as a bolus; as an electuary; or as a paste.

The invention also provides a food-stuff intended for dieters which is, or comprises, a foodstuff of the invention. The invention provides for the use of the products described herein for slimming, dieting or weight reduction. The invention also provides for products for diabetics comprising, or consisting of, a foodstuff of the invention. In one instance, the invention provides a diabetic chocolate, where the chocolate is a chocolate of the invention.

In one preferred instance, a foodstuff of the invention may be provided with packaging and/or wrapping. Such packaging/wrapping may indicate the benefits of the invention and/or suggest consumption at, or near, mealtimes for maximal benefit. The packaging/wrapping may indicate the benefits of the product in slimming, decreasing cholesterol, and/or triglyceride levels. In another instance, the packaging may refer to the ability of the product to improve oxygen transport. The packaging may refer to treating or ameliorating any of the conditions mentioned herein. The packaging may be a sachet, for instance where the product is to be made up as a beverage.

The invention also provides food products targeted at sports people. For instance, the products may be used to reduce weight in such subjects or bring about any of the other benefits highlighted herein for the products of the invention. The products may be packaged or wrapped and include an indication of their ability to increase oxygen transport. The products of the invention may be used to reduce recovery time. The products may be used by climbers, particularly those climbing at altitude.

In addition to cocoa-bean products, food products described herein comprise a carotenoid compound.

The carotenoid compound may be isolated in the products of the invention. An isolated carotenoid compound is outside the physical milieu or environment in which it occurs in nature. For example, an isolated carotenoid compound may be free or substantially free from its natural environment e.g. it is not contained in the natural plant material with which it is naturally associated. Isolated carotenoid compounds include compounds which have been isolated, concentrated, purified or partially purified from natural sources, such as plants, and compounds which have been produced synthetically.

The food product will typically provide an effective amount of carotenoid, such as lycopene. The food product may comprise 0.0001% to 1%; 0.001% to 1%; or 0.01% to 0.1% by weight of carotenoid compound. For example, the food product may comprise 0.001 to 10 mg of carotenoid compound per one gram of food product, for example, 0.01 to 10 mg per gram or 0.1 to 1 mg per one gram of food product. The product of the invention will typically provide an effective amount of the carotenoid, for instance an amount effective to alter one of the parameters referred to herein.

The food product may be in a unit dose form which allows a controlled daily dose of carotenoid, preferably lycopene, to be consumed. For example, the food product may be formulated to provide a daily dose of 0.1 mg to 100 mg of lycopene, preferably 0.5 to 50 mg of lycopene. In some instances, a product of the invention may provide about 0.1 mg, 0.2 mg, 0.5 mg, 1 mg, 1.5 mg, 2 mg, 2.5 mg or more of carotenoid, such as about 3, 4, 5, 6, 7, 8, 9, or 10 mg of carotenoid. In some instances, the amount of carotenoid may be about 10, 15, 20 or 25 mg, or up to those levels. Preferably the carotenoid is lycopene. The product may comprise an amount of carotenoid which is in a range with any two of the values mentioned herein as endpoints.

In one instance, the foodstuff or product provides from 0.1 to 1.0 mg of carotenoid per gram of food product for example at least 0.2, 0.3, 0.4 or 0.5 mg carotenoid per gram of food product, with in some instances, up to 0.3, 0.4, 0.5, 0.6, 0.7, 0.8, 0.9 or 1.0 mg of carotenoid per gram of product. In one preferred instance, those values are employed where the product is chocolate and/or carotenoid is lycopene, preferably both. In another instance, the level of foodstuff administered is enough to reduce any of the makers discussed herein, preferably to near, or at, or below baseline levels for a healthy control or below baseline prior to administration of the product.

In some instances, the ratio of carotenoid to triglyceride or other fat molecules in the products of the invention may be from 1:1000 to 1:100,000, for instance from 1:2000 to 1:50,000, or from 1:5000 to 1:25,000.

The carotenoid and cocoa bean product may be present in a synergistic amount. For instance, they may be present where the combination produces a greater effect on any of the parameters mentioned herein than either individually when provided in the same amount. The invention therefore also provides a synergistic combination of a carotenoid and cocoa bean product. The invention also provides for the use of a carotenoid, such as any of those referred to herein, to treat any of the conditions mentioned herein, where the subject is also being administered chocolate and also the use of chocolate to treat any of the conditions mentioned herein where the subject is also being administered a carotenoid. Typically the carotenoid and chocolate will be administered together, for instance eaten together, or within 5, 10, 15, 30, 45 or 60 minutes of each other. The two may be given simultaneously.

Carotenoid compounds are tetraterpenoids which contain long polyene chains. Carotenoid compounds include xanthophylls such as lutein, capsanthin and zeaxanthin, and carotenes, such as beta-carotene, alpha-carotene, zeto-carotene, and lycopene compounds.

Lycopene compounds may include lycopene, 1-HO-3',4'-didehydrolycopene, 3,1'-(HO)2-gamma-carotene, 1,1'-(HO)2-3,4,3',4'-tetradehydrolycopene, 1,1'-(HO)2-3,4-didehydrolycopene.

In preferred embodiments, the carotenoid compound is lycopene.

Lycopene is an open-chain unsaturated $C_{40}$ carotenoid of structure I (Chemical Abstracts Service Registry Number 502-65-8), Structure I

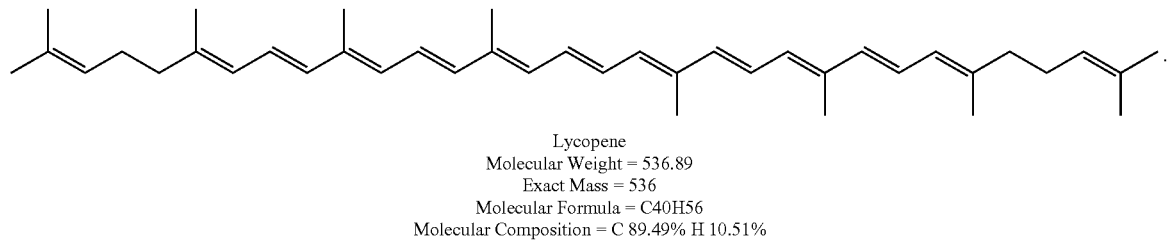

Lycopene
Molecular Weight = 536.89
Exact Mass = 536
Molecular Formula = C40H56
Molecular Composition = C 89.49% H 10.51%

Lycopene occurs naturally in plants such as tomatoes, guava, rosehip, watermelon and pink grapefruit and any such sources of lycopene may be, for instance, employed.

Lycopene for use as described herein may comprise one or more different isomers. For example, lycopene may include cis-lycopene isomers, trans-lycopene isomers and mixtures of the cis- and trans-isomers. Lycopene may comprise at least 10%, at least 20%, at least 30%, at least 40%, at least 50%, at least 60%, at least 70%, at least 80%, at least 90%, or at least 95% (Z)-isomers, (all-E)-isomers, or cis-isomers, such as 5-cis- or 9-cis- or 13-cis-isomers, which have improved bioavailability relative to trans isomers. Trans isomers may isomerise into cis forms in vivo, or during storage and processing.

Carotenoid compounds, such as lycopene, for use as described herein may be natural i.e. obtained from a natural source, for example, extracted from a plant, such as a tomato or melon. In one instance, oleoresin, particularly tomato oleoresin, may be employed in the invention. A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed.

Carotenoid compounds, such as lycopene, for use as described herein may be synthetic i.e. produced by artificial means, for example, by chemical synthesis. A range of methods for chemical synthesis of lycopene and other carotenoids are known in the art.

For example, a three-stage chemical synthesis based on the standard Wittig olefination reaction scheme for carotenoid synthesis may be employed, in which an organic solution of $C_{15}$ phosphonium methanesulfonate in dichloromethane (DCM) and an organic solution of $C_{10}$ dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then be heated and cooled to crystalline slurry that is filtered and washed with methanol. The lycopene crystals may then be recrystallized and dried under heated nitrogen. Synthetic carotenoids, such as lycopene, are also available from commercial suppliers (e.g. BASF Corp, NJ USA).

Synthetic carotenoid compounds, such as lycopene, may comprise an increased proportion of cis isomers relative to natural carotenoid compounds. For example, synthetic lycopene may be up to 25% 5-cis, 1% 9-cis, 1% 13-cis, and 3% other cis isomers, whilst lycopene produced by tomatoes may be 3-5% 5-cis, 0-1% 9-cis, 1% 13-cis, and <1% other cis isomers. Since cis-lycopene has increased bioavailability relative to trans-lycopene, synthetic lycopene is preferred in some embodiments.

Derivatives of carotenoids as described above may be produced by chemical synthesis analogous to the synthesis described above or by chemical modification of natural carotenoids extracted from plant material.

A food product as described herein may contain a single carotenoid compound (e.g. lycopene) or more than one carotenoid compound (e.g. lycopene and beta-carotene). Typically, each carotenoid compound will be present in a range of different isomeric forms.

The food product may be produced by admixing or blending the cocoa-bean products, such as cocoa butter and cocoa solids, and optionally one or more other ingredients, and the carotenoid compound under conditions which allow the carotenoid compound to incorporate into the matrix of the food product.

Other ingredients may include sugar, vanilla, milk, milk powder, emulsifying agents, such as soy lecithin or polyglycerol polyricinoleate (PGPR; E476), whey or potato peptides and/or proteins, soy products, such as soy proteins, soy extracts and/or soy isoflavones, vegetable oils or animal fats, nut-based products, such as nut powders and nut extract, starch and polysaccharides.

The cocoa-bean products may be in a dry, liquid, aerosol, frozen or melted form for admixing or blending with the carotenoid compound. For example, chocolate for blending may be in liquid form (i.e. melted chocolate).

In some preferred embodiments, the cocoa-bean products and the carotenoid compound in mixable forms and have the same or similar viscosities.

Suitable methods of mixing and blending, including mechanical blending, are well-known in the art.

In one instance, a carotenoid is added whilst the chocolate is being made or chocolate is melted and the carotenoid added. The chocolate may be added to a mould to give products of a particular shape and/or size.

The invention also provides for a method of producing a food product, such as a food product of the invention, which comprises adding a carotenoid during production of the food product. For instance, the carotenoid may be added during the preparation of chocolate.

Products of the invention may also contain other ingredients such as flavourings, emulsifiers, colourings and/or preservatives. In some cases the products may comprise nuts, particularly where the product is a chocolate, such as walnuts, hazelnuts, almonds or brazil nuts.

Food products as described herein are shown to have an unexpected effect on levels of blood cholesterol, low density lipoprotein, triglycerides and/or other lipids or lipid particles, such as LDL particles, in an individual. Given chocolate is perceived as a high fat food, that was unexpected.

Aspects of the invention provide a food product as described above for use in reducing blood levels of cholesterol, low density lipoprotein, triglycerides and/or other lipids or lipid particles, such as LDL particles, in an individual and a method of reducing blood levels of cholesterol, low density lipoprotein, triglycerides and/or other lipids or lipid particles, such as LDL particles, in an individual comprising administering a food product described above to the individual.

Another aspect of the invention provides the use of a carotenoid compound and one or more cocoa bean products, as described above, in the manufacture of a food product for use in reducing blood levels of cholesterol, low density lipoprotein, triglycerides and/or other lipids or lipid particles, such as LDL particles, in an individual.

This may be useful in the treatment or prevention of cardio- and cerebro-vascular disorders, or Metabolic Syndrome, high blood pressure, pre-diabetes and type II diabetes, being overweight (e.g. BMI>25), obesity (e.g. BMI>30) and hypercholesterolaemia. The invention may be employed, for instance, with any of those subjects. The products of the invention may be used in dieting.

The invention also provides a method of dieting comprising consuming a product of the invention as part of the diet.

An individual is preferably a human, though use in animals is also possible. The individual may have normal blood levels of cholesterol, LDL and/or triglycerides or elevated blood levels of cholesterol, LDL and/or triglycerides. In some instances, the subject may have a total serum cholesterol of more than 200 mg/dL, for instance more than 210 mg/dL. In some cases a subject may additionally, or alternatively have, triglyceride levels above 150 mg/dL. In some cases, the subject may be apparently healthy, but be identified as having such elevated levels of cholesterol and/or triglycerides, in other instances the subject may have a history of heart disease and/or atherosclerosis. The subject may be overweight and may be obese. The subject may be one taking statins, aspirin and/or blood pressure reducing medication. The subject may be one on a diet.

Methods of measuring levels of cholesterol, LDL, triglycerides and other lipids in an individual are well-known in the art.

In some embodiments, the individual may be at suffering from, or at risk of suffering from, a cardio- or cerebro-vascular disorders, such as coronary heart disease, metabolic syndrome, high blood pressure, pre-diabetes and type II diabetes, being overweight (e.g. BMI>25) or obesity (e.g. BMI>30). The subject may have had a heart attack. The subject may have had a stoke.

Food products as described herein are also shown to reduce levels of markers of inflammatory oxidative damage in an individual. In some cases the subject may have elevated levels of inflammatory oxidative damage. For instance, they may have ≥20-39 μM MDA and/or at least 0.25 to 0.30 u/ml of $P_x$-IgG Such levels may be in addition to, or alternative to, the above specified levels of total cholesterol and/or triglycerides.

The food products may therefore also be useful in reducing inflammation; reducing anti-inflammatory oxidative damage; increasing antioxidant activity and/or reducing or delaying symptoms of aging in an individual. The invention may be used to reduce the visible signs of aging.

Examples of possible daily doses of 0.1 mg to 100 mg of carotenoid compound, such as lycopene, preferably 0.5 to 50 mg, may be administered to the individual. Any of the amounts referred to herein may be administered.

In some embodiments, a suitable individual may be a mature or elderly individual, for example at least 50, 60, 65, 70, 75 or more years old or be of an age in the range defined by any of those two values.

Food products as described herein may also be useful in providing nutrition to an individual.

For example, food products may be useful as sports nutrition products or in providing nutrition to mature or elderly individuals (e.g. >50 years old) or individuals undergoing body mass control or reduction, i.e. for "slimming" purposes.

In other examples, food products may be useful in providing nutrition to individual having or recovering from a clinical condition. For example, food products described herein may be useful in the nutrition of an individual recovering from injury, operation, or trauma; an individual having or recovering from chemo- or radio-therapy; or an individual having or at risk of Metabolic Syndrome, obesity, diabetes II, atherosclerosis and their clinical complications.

The invention may be used to help treat ischemia or hypoxia. The invention may be, in some instances, administered after blood flow has been cut off to a particular tissue or organ. In one instance, the invention may be administered to subjects who have had a stroke.

Food products as described herein may also be useful in the treatment or prevention of cardio- and cerebro-vascular disorders, hypertension, metabolic syndrome, high blood pressure, pre-diabetes and type II diabetes, being overweight (e.g. BMI>25), obesity (e.g. BMI>30) or other medical conditions such as anaemia, rheumatism, rheumatoid arthritis, non-rheumatoid arthritis, prostate or testes malfunctions, erectile dysfunctions, loss of libido, cellulite, sarcopenia and cachexia.

In some instances, the subject the invention is applied to may have an auto-immune disease; an allergic condition; hypertension; atherosclerosis; cardio pathologies, such as Coronary Heart Disease; vascular pathologies, such as endocarditis, myocarditis, heart failure, heart valve disease, arrhythmias, atherosclerosis, hypertension, vasculitis, endarteritis, varicose veins, endophlebitis, endothelial damage; cerebral pathologies; obesity; diabetes type 2; cancer, sarcopenia; metabolic dysfunction; Metabolic Syndrome; cellulite and aging tissue degradation; gastritis; stomach or duodenum ulcers; or arthritis; or dermatitis, psoriasis, acne, chronic skin ulcerations, or other age-related or not skin conditions, including skin and other tissues burns and wounds; sport, trauma, operation and other injuries; cachexia, side-effects of chemotherapies and radiation treatment, or radiation exposure; the subject may be at risk of such a condition.

Due to the ability of the invention to increase oxygen transport, the invention may also be used to treat conditions where such increased oxygen transport may be beneficial. For instance, a subject with a respiratory disorder such as emphysema, COPD, cystic fibrosis, asthma, or ARDS. The subject may have reduced lung function, for instance due to lung damage or lung cancer. In one instance, the subject may be a smoker.

The invention may also be used to treat impairment of tissue oxygenation, for instance due to reduction of blood supply due to circulatory dysfunction or circulatory disease. The subject may have had an injury, disease or disorder causing reduced blood flow, for instance one that results from blood flow to an organ and/or tissue being reduced or cut-off.

The invention may be used to increase tissue oxygenation and treat circulatory disease. In one instance the circulatory disorder may be due to traumatic, compressive, occlusive, tumors/malformations and/or vasospastic reduction in oxygenation. The subject may have atherosclerosis resulting in reduced tissue oxygenation or DVT. The subject may be one with angina, such as angina pectoris, acute coronary syndrome, or had a myocardial infraction. The invention may also be used to treat individuals with reduced tissue inflammation due to ongoing inflammatory conditions or processes in the tissue, such as any of those referred to herein.

Given the ability of the invention to reduce inflammatory markers, the invention may also be employed to help treat inflammatory or autoimmune disorders, for instance arthritis, inflammatory bowel disease and atherosclerosis.

Another aspect of the invention provides a nutracosmetic formulation comprising one or more cocoa bean products and a carotenoid compound.

Suitable cocoa bean products and carotenoid compounds are described in more detail above.

A nutracosmetic formulation which comprises one or more cocoa bean products and a carotenoid compound as defined above, may further comprise one or more cosmetically or nutritionally acceptable carriers, adjuvants, excipients, sweeteners, diluents, fillers, buffers, stabilisers, preservatives, colourings, lubricants, or other materials well known to those skilled in the art.

The term "nutraceutically acceptable" as used herein pertains to compounds, materials, compositions, and/or dosage forms which are in common or widespread usage in food and dietary products and are generally considered non-toxic, for example, compounds may have the US FDA designation "GRAS" (Generally Recognised as Safe), or equivalent food additive status in other jurisdictions.

Nutracosmetic formulations are generally intended for oral administration and may be formulated accordingly.

Nutracosmetic formulations may be useful in improving the appearance of an individual or in reducing, delaying or masking Visual signs of aging in an individual.

The invention may be administered to treat, ameliorate, prevent, or reduce the severity of symptoms in any of the conditions referred to herein. In one instance, the invention is administered prophylatically to help prevent the onset of any of the conditions mentioned herein. The invention may result in reduction of any of the parameters discussed herein, it may, for instance, reduce cholesterol, triglyceride, inflammatory damage, weight or body fat.

Various further aspects and embodiments of the present invention will be apparent to those skilled in the art in view of the present disclosure.

All documents mentioned in this specification are incorporated herein by reference in their entirety.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

In instances herein where the terms "comprises" or "comprising" are used, the invention may also provide what is described when it "consists essentially of" or "consisting of" the specified constituents.

Unless context dictates otherwise, the descriptions and definitions of the features set out above are not limited to any particular aspect or embodiment of the invention and apply equally to all aspects and embodiments which are described.

The following is a list of some further numbered embodiments of the invention:

(1) A food product comprising one or more cocoa bean products and an isolated carotenoid compound.

(2) A food product according to (1) which comprises a homogenous matrix containing the cocoa-bean products and the carotenoid compound.

(3) A food product according to (1) or (2) wherein the cocoa bean products comprise one or more of cocoa solids, cocoa powder, cocoa liquor and/or cocoa butter.

(4) A food product according to any of (1) to (3) where the one or more cocoa bean products are in the form of a chocolate or cocoa butter matrix, said matrix incorporating the carotenoid compound.

(5) A food product according to any one (1) to (4) which comprises 0.001 to 10 mg of carotenoid compound per gram of food product.

(6) A food product according to any one of (1) to (5) the wherein the carotenoid compound is a lycopene compound.

(7) A food product according to any one of (1) to (6) wherein the carotenoid compound is comprised in a carotenoid-rich product, such as tomato or other fruit, vegetable or plant paste, sauce, concentrate, oleoresin, fraction or extract.

(8) A food product according to any one of (1) to (6) wherein the carotenoid compound is comprised in a carotenoid rich fruit, vegetable or other plant, or fungus, algae or bacterium.

(9) A food product according to any one of (1) to (8) wherein the lycopene compound is lycopene.

(10) A food product according to any one of (1) to (8) wherein the food product is produced by admixing or blending together the cocoa bean products, the carotenoid compound and optionally one or more additional ingredients.

(11) A food product according to (10) wherein the cocoa bean products are admixed or blended together with the carotenoid compound in a dry, liquid, aerosol, frozen or melted form.

(12) A food product according to any one of (1) to (11) wherein the food product is a foodstuff.

(13) A food product according to (12) wherein the foodstuff is bread, flour, cereal, biscuit, pastry, spread, filling, paste, sauce, mousse, cream, or yogurt.

(14) A food product according to (12) wherein the foodstuff is a confectionery product.

(15) A food product according to (14) wherein the foodstuff is chocolate.

(16) A food product according to (15) wherein the chocolate is dark, milk, or white chocolate.

(17) A food product according to any one of (1) to (11) wherein the food product is a beverage.

(18) A food product according to any one of (1) to (11) wherein the food product is a dietary supplement, nutracosmetic or nutraceutical product.

(19) A food product according to any one of (1) to (18) for use in reducing levels of cholesterol, LDL and/or triglyceride in an individual.

(20) A food product according to any one of (1) to (19) for use in reducing inflammation; reducing anti-inflammatory oxidative damage; increasing antioxidant activity and/or reducing or delaying symptoms of aging in an individual.

(21) A food product according to any one of (1) to (20) for use in the nutrition of an individual.

(22) A food product for use according to (21) wherein the individual is mature or elderly.

(23) A food product: for use according to any one of (19) to (22) wherein the individual is undergoing body mass control or body mass reduction.

(24) A food product for use according to any one of (19) to (22) wherein the individual is suffering from; at risk of suffering from; or recovering from a clinical condition.

(25) A food product for use according to (24) wherein the individual is recovering from injury, operation, or trauma or undergoing or recovering from chemo- or radio-therapy; or having or being at risk of having Metabolic Syndrome, obesity, diabetes II, atherosclerosis and clinical complications thereof.

(26) A food product for use according to any one of (1) to (20) for the treatment of a clinical condition.

(27) A food product for use according to (26) wherein the clinical condition is a cerebro-vascular disorder, cardio-vascular disorder, hypertension, metabolic syndrome, high blood pressure, pre-diabetes, type II diabetes, being overweight (e.g. BMI>25), obesity (e.g. BMI>30), anaemia, rheumatism, rheumatoid arthritis, non-rheumatoid arthritis, prostate or testes malfunction, erectile dysfunction, loss of libido, cellulite, sarcopenia and cachexia.

(28) A method of improving the appearance of an individual comprising administering a nutracosmetic formulation according to any one of (1) to (18) to the individual.

(29) A method of reducing or delaying visible signs of aging in an individual comprising administering a nutracosmetic formulation according to any one of (1) to (18) to the individual.

(30) A method of reducing levels of cholesterol, LDL and/or triglyceride in the blood of an individual comprising administering a food product according to any one of (1) to (18) to an individual in need thereof.

(31) A method of reducing inflammation; reducing anti-inflammatory oxidative damage; increasing antioxidant activity and/or reducing or delaying symptoms of aging in an individual; comprising administering a food product according to any one of (1) to (18) to an individual in need thereof.

(32) A method of providing nutrition to an individual comprising administering a food product according to any one of (1) to (18) to an individual in need thereof.

(33) A method according to (32) wherein the individual is mature or elderly.

(34) A method according to any one of (30) to (33) wherein the individual is undergoing body mass control or body mass reduction.

(35) A method according to any one of (30) to (33) wherein the individual is suffering from; at risk of suffering from; or recovering from a clinical condition.

(36) A method according to (35) wherein the individual is recovering from injury, operation, or trauma or undergoing or recovering from chemo- or radio-therapy; or having or being at risk of having Metabolic Syndrome, obesity, type II diabetes, atherosclerosis and clinical complications thereof.

(37) A method of treatment: of a clinical condition comprising administering a food product according to any one of (1) to (18) to an individual in need thereof.

(38) A method of treatment according to (37) wherein the clinical condition is cerebra-vascular disorder, cardio-vascular disorder, hypertension, metabolic syndrome, high blood pressure, pre-diabetes, type II diabetes, being overweight (e.g. BMI>25), obesity (e.g. BMI>30), anaemia, rheumatism, rheumatoid arthritis, non-rheumatoid arthritis, prostate or testes malfunction, erectile dysfunction, loss of libido, cellulite, sarcopenia or cachexia.

Certain aspects and embodiments of the invention will now be illustrated by way of example and with reference to the tables described below.

Table 1 shows the effect of lycopene on lipid parameters, and markers of IOD and inflammation in CHD patients.

Table 1 shows the effect of 30 g dark chocolate on lipid parameters, and markers of IOD and inflammation in CHD patients.

Table 3 shows the effect of 30 g of L-chocolate on lipid parameters, and markers of IOD and inflammation in CHD patients.

The results presented in the other Tables are discussed in the individual Examples below.

EXAMPLES

Experiments

Lipid-Lowering Chocolate (L-Chocolate)

Commercially available dark chocolate (Green & Black's Dark Chocolate; 85% cocoa) was melted at 70° C. The melted chocolate was mixed with tomato oleoresin, containing 15% of lycopene (Lyc-O-Mato), in the ratio of 1.57 mg of oleoresin to 1 g of the chocolate. The mixture was blended for 10 minutes and then divided into daily 10 g or 30 g portions and cooled down to the room temperature.

Each 10 g or 30 g chocolate portion contained 47.1 mg of tomato oleoresin or about 7 mg of lycopene.
Control Samples of Chocolate The melting and mixing procedures were performed as described above using the same commercially available dark chocolate, but instead of tomato oleoresin, sunflower oil (Floral™) was used.
Lycopene 47.1 mg of tomato oleoresin was pre-dissolved in ethanol and mixed with Whey Protein as described in Richelle et al (2002) *J Nutr* 132 404-408, WO01/091588 and US2002/01072992. Then the mixture was placed into gelatine capsules.

All products were kept in cool dry, protected from light conditions.
Validation in Clinical Trials
CHD Patients 18 male CHD patients, age 47-69, were recruited for this study.

Main inclusion criteria were:
elevated total serum cholesterol above 200 mg/dL and/or triglycerides above 150 mg/dL,
all patients were naive for any lipid-lowering medications,
stable clinical conditions and regimen of medications was t the last 3 months.

Secondary inclusion criteria were:
positive blood markers on inflammatory oxidative damage, IOD, >20-30 µM MDA
positive blood on an antibody inflammatory marker, Px-IgG>0.250-0.300 U/ml All patients were randomised and divided into three equal groups of 6 patients each. Two groups receiving chocolate were blinded; the group receiving lycopene preparation along was open labelled. The period of the trial was 4 weeks.
Results The results of the ongoing trial are presented in the tables 1 to 3 below.

It was observed that after two weeks of administration of 7 mg of lycopene, there were no changes in any patients on their levels of elevated cholesterol, triglycerides and markers of oxidative damage or inflammation (table 1).

Similar results were observed in the group where patients were taking 30 g of the control bar of dark chocolate (table 2).

However, in the group of patients taking 30 g of L-chocolate, a reduction in concentration of both total cholesterol and its LDL fraction was observed in every patient in the group even after the first seven days of the trial (table 3). The positive trend in triglyceride levels was also detected in 5 out of 6 patients.

Furthermore, the elevated level of transferases in two patients in this group also started to decline, indicating a positive effect of L-chocolate on their liver damage status. In addition, for the majority of the patients administration of the L-chocolate was accompanied by reduction of inflammatory oxidative damage markers, indicating that this product has not only lipid-lowering properties but anti-inflammatory as well.

TABLE 1

| | | | | Lycopene | | | | | | |
|---|---|---|---|---|---|---|---|---|---|---|
| ID | Age | IOD µM MDA | Px-IgG U/ml | TC mg/dL | TG mg/dL | HDL mg/dL | LDL mg/dL | GL mmol/L | AST U/L | ALT U/L |
| | | | | Baseline | | | | | | |
| 13 | 48 | 101 | 0 765 | 225 | 161 | 39 | 153 | 6.5 | 44 | 25 |
| 14 | 69 | 162 | 0.698 | 231 | 150 | 42 | 159 | 5.6 | 45 | 36 |
| 15 | 54 | 79 | 0.811 | 204 | 134 | 41 | 135 | 3.8 | 34 | 24 |
| 16 | 49 | 95 | 0.803 | 219 | 126 | 44 | 161 | 4.4 | 27 | 35 |
| 17 | 66 | 83 | 0.751 | 243 | 165 | 37 | 186 | 5.9 | 49 | 29 |
| 18 | 53 | 49 | 0.743 | 210 | 157 | 40 | 147 | 6.1 | 25 | 26 |
| | 56.5 | 95 | 0.762 | 222 | 149 | 40.5 | 157 | 5.4 | 37.3 | 29.2 |
| | | | | Week 1 | | | | | | |
| 13 | 48 | 99 | 0.823 | 224 | 160 | 39 | 153 | 6.4 | 47 | 31 |
| 14 | 69 | 158 | 0.746 | 231 | 152 | 42 | 160 | 5.7 | 46 | 33 |
| 15 | 54 | 85 | 0.809 | 205 | 137 | 40 | 134 | 4.9 | 36 | 29 |

TABLE 1-continued

Lycopene

| ID | Age | IOD μM MDA | Px-IgG U/ml | TC mg/dL | TG mg/dL | HDL mg/dL | LDL mg/dL | GL mmol/L | AST U/L | ALT U/L |
|---|---|---|---|---|---|---|---|---|---|---|
| 16 | 49 | 94 | 0.867 | 217 | 130 | 43 | 160 | 3.6 | 31 | 34 |
| 17 | 66 | 81 | 0.851 | 241 | 164 | 38 | 185 | 5.1 | 44 | 33 |
| 18 | 53 | 57 | 0.839 | 209 | 159 | 40 | 149 | 6.1 | 34 | 29 |
|  |  | 96 | 0.823 | 221 | 150 | 40.3 | 157 | 5.3 | 39.7 | 31.5 |

Week 2

| 13 | 48 | 95 | 0.812 | 223 | 159 | 39 | 152 | 6.6 | 43 | 29 |
| 14 | 69 | 139 | 0.809 | 230 | 151 | 41 | 158 | 5.2 | 42 | 31 |
| 15 | 54 | 84 | 0.815 | 208 | 138 | 40 | 133 | 5.4 | 31 | 28 |
| 16 | 49 | 91 | 0.844 | 216 | 132 | 42 | 159 | 4.1 | 38 | 32 |
| 17 | 66 | 75 | 0.830 | 239 | 162 | 39 | 183 | 3.9 | 41 | 31 |
| 18 | 53 | 68 | 0.799 | 208 | 158 | 41 | 150 | 6 | 30 | 34 |
|  |  | 92 | 0.818 | 221 | 150 | 40.3 | 156 | 5.2 | 37.5 | 30.8 |

Week 3

| 13 | 48 | 94 | 0.834 | 221 | 155 | 39 | 151 | 6.2 | 42 | 32 |
| 14 | 69 | 136 | 0.781 | 227 | 149 | 42 | 157 | 4.8 | 39 | 29 |
| 15 | 54 | 85 | 0.84 | 210 | 135 | 40 | 132 | 5.1 | 35 | 25 |
| 16 | 49 | 93 | 0.795 | 214 | 142 | 41 | 155 | 5 | 36 | 31 |
| 17 | 66 | 76 | 0.809 | 232 | 161 | 38 | 179 | 4.4 | 42 | 28 |
| 18 | 53 | 81 | 0.774 | 211 | 154 | 41 | 152 | 5.8 | 33 | 31 |
|  |  | 94 | 0.806 | 219 | 149 | 40.2 | 154 | 5.22 | 37.8 | 29.3 |

TABLE 2

Chocolate

| ID | Age | IOD μM MDA | Px-IgG U/ml | TC mg/dL | TG mg/dL | HDL mg/dL | LDL mg/dL | GL mmol/L | AST U/L | ALT U/L |
|---|---|---|---|---|---|---|---|---|---|---|

Baseline

| 7 | 49 | 132 | 0.902 | 209 | 165 | 41 | 157 | 5.6 | 35 | 25 |
| 8 | 55 | 96 | 0.933 | 232 | 183 | 40 | 153 | 4.2 | 42 | 36 |
| 9 | 51 | 145 | 0.998 | 198 | 182 | 45 | 124 | 6.6 | 28 | 24 |
| 10 | 62 | 53 | 0.756 | 227 | 144 | 39 | 179 | 5.9 | 41 | 35 |
| 11 | 50 | 61 | 0.854 | 217 | 136 | 41 | 166 | 3.8 | 33 | 29 |
| 12 | 53 | 110 | 0.941 | 221 | 179 | 38 | 148 | 5.8 | 37 | 26 |
|  | 53.3 | 99.5 | 0.897 | 217 | 165 | 40.7 | 155 | 5.3 | 36 | 29.2 |

Week 1

| 7 | 49 | 123 | 0.912 | 208 | 168 | 41 | 156 | 5.8 | 37 | 27 |
| 8 | 55 | 105 | 0.875 | 229 | 181 | 40 | 154 | 4.9 | 41 | 43 |
| 9 | 51 | 132 | 0.914 | 201 | 178 | 44 | 128 | 6.4 | 35 | 28 |
| 10 | 62 | 96 | 0.665 | 225 | 149 | 40 | 177 | 5.9 | 40 | 38 |
| 11 | 50 | 83 | 0.806 | 216 | 147 | 42 | 165 | 4.7 | 36 | 31 |
| 12 | 53 | 105 | 0.915 | 219 | 180 | 38 | 149 | 5.6 | 39 | 30 |
|  |  | 107 | 0.848 | 216 | 167 | 40.8 | 155 | 5.5 | 38 | 32.3 |

Week 2

| 7 | 49 | 119 | 0.945 | 207 | 169 | 40 | 157 | 5.9 | 32 | 29 |
| 8 | 55 | 99 | 0.927 | 230 | 179 | 40 | 154 | 5.6 | 39 | 44 |
| 9 | 51 | 141 | 0.983 | 197 | 185 | 45 | 126 | 6.4 | 29 | 32 |
| 10 | 62 | 67 | 0.844 | 223 | 155 | 40 | 176 | 5.8 | 42 | 37 |
| 11 | 50 | 78 | 0.915 | 218 | 146 | 41 | 165 | 3.7 | 35 | 33 |
| 12 | 53 | 114 | 0.926 | 215 | 182 | 39 | 147 | 5.9 | 35 | 35 |
|  |  | 103 | 0.923 | 215 | 169 | 40.8 | 154 | 5.55 | 35.3 | 35 |

Week 3

| 7 | 49 | 118 | 0.999 | 201 | 165 | 40 | 156 | 5.2 | 32 | 28 |
| 8 | 55 | 99 | 0.876 | 233 | 182 | 41 | 157 | 4.9 | 39 | 43 |
| 9 | 51 | 133 | 0.858 | 195 | 164 | 44 | 134 | 6.7 | 29 | 36 |
| 10 | 62 | 69 | 0.761 | 219 | 153 | 41 | 175 | 5.1 | 42 | 47 |
| 11 | 50 | 83 | 0.944 | 226 | 132 | 42 | 161 | 4.2 | 35 | 31 |
| 12 | 53 | 105 | 0.832 | 209 | 167 | 38 | 149 | 5 | 35 | 37 |
|  |  | 101 | 0.878 | 214 | 160 | 41 | 155 | 5.2 | 35.3 | 37 |

TABLE 3

| | | | Chocolate + Lycopene | | | | | | | |
|---|---|---|---|---|---|---|---|---|---|---|
| ID | Age | IOD µM MDA | Px-IgG U/ml | TC mg/dL | TG mg/dL | HDL mg/dL | LDL mg/dL | GL mmol/L | AST U/L | ALT U/L |
| | | | | Baseline | | | | | | |
| 1 | 52 | 73 | 0 904 | 217 | 121 | 40 | 132 | 4.5 | 22 | 40 |
| 2 | 55 | 46 | 0.842 | 211 | 200 | 37 | 169 | 4.7 | 30 | 33 |
| 3 | 63 | 88 | 0.871 | 249 | 199 | 42 | 174 | 5.3 | 30 | 27 |
| 4 | 59 | 150 | 0.901 | 136 | 170 | 37 | 167 | 6.2 | 48 | 110 |
| 5 | 47 | 112 | 0.660 | 228 | 168 | 40 | 150 | 4.6 | 40 | 45 |
| 6 | 49 | 123 | 0.789 | 227 | 113 | 42 | 130 | 5.5 | 120 | 154 |
| | 54 | 98.7 | 0.827 | 211 | 162 | 39.7 | 154 | 5.1 | 48.7 | 68.2 |
| | | | | Week 1 | | | | | | |
| 1 | 52 | 76 | 0.943 | 195 | 120 | 40 | 130 | 4.2 | 22 | 40 |
| 2 | 55 | 38 | 0.912 | 183 | 200 | 37 | 167 | 4.8 | 30 | 32 |
| 3 | 63 | 69 | 0.838 | 233 | 179 | 42 | 170 | 5 | 30 | 26 |
| 4 | 59 | 143 | 0.522 | 132 | 162 | 37 | 162 | 6.1 | 49 | 73 |
| 5 | 47 | 97 | 0.720 | 208 | 161 | 40 | 149 | 4.4 | 38 | 42 |
| 6 | 49 | 101 | 0.324 | 193 | 99 | 42 | 127 | 5 | 74 | 137 |
| | | 87.3 | .710 | 191 | 153 | 39.7 | 151 | 4.9 | 40.5 | 58.3 |
| | | | | Week 2 | | | | | | |
| 1 | 52 | 44 | 0.452 | 193 | 119 | 40 | 129 | 4.3 | 22 | 40 |
| 2 | 55 | 19 | 0.81 | 183 | 202 | 37 | 167 | 4.7 | 27 | 36 |
| 3 | 63 | 58 | 0.448 | 223 | 178 | 42 | 170 | 5.1 | 30 | 28 |
| 4 | 59 | 63 | 0 522 | 130 | 161 | 37 | 160 | 6.2 | 45 | 70 |
| 5 | 47 | 88 | 0.23 | 200 | 159 | 40 | 147 | 4.5 | 38 | 41 |
| 6 | 49 | 89 | 0.214 | 191 | 89 | 42 | 125 | 5.8 | 70 | 132 |
| | | 60.2 | 0.446 | 187 | 151 | 39.7 | 150 | 5.1 | 38.7 | 57.8 |
| | | | | Week 3 | | | | | | |
| 1 | 52 | 53 | 0.129 | 193 | 119 | 40 | 129 | 4.3 | 22 | 40 |
| 2 | 55 | 21 | 0.742 | 182 | 188 | 38 | 160 | 4.5 | 27 | 35 |
| 3 | 63 | 41 | 0.081 | 225 | 171 | 42 | 170 | 5-2 | 30 | 27 |
| 4 | 59 | 50 | 0.096 | 130 | 158 | 38 | 159 | 6.1 | 44 | 70 |
| 5 | 47 | 61 | 0 | 189 | 154 | 40 | 137 | 5.0 | 38 | 39 |
| 6 | 49 | 54 | 0.120 | 190 | 84 | 43 | 122 | 5.5 | 72 | 130 |
| | | 46.7 | 0.195 | 185 | 146 | 40.1 | 146 | 5.1 | 38.1 | 56.8 |

Clinically Healthy Volunteers with Hypercholesterolaemia Dose Effect 52 clinically healthy volunteers 26 males and 26 females, age 35-61 years old, were recruited for this study.

Main inclusion criteria were:
elevated total serum cholesterol above 200 mg/dL and/or triglycerides above 150 mg/dL,
all patients were naive, for at least 3 months prior to the study, for any lipid-lowering medications, dietary supplements or special lipid or weight management diets,
willing participate in the study.

All volunteers were randomised and divided into six groups. 10 participants were included in the control group and group which received chocolate containing 0.36 mg of lycopene per 1 gram of the product. Other four groups were formed from 8 volunteers each. Every participant received the one week supply of the same size of 10 g of the chocolate bar with different concentration of lycopene, or without it at all.

All chocolate samples were blinded so participants did not know what exactly composition of chocolate they were ingesting. All collected blood samples were also blinded so the analytical laboratory was not aware from which volunteers and from which group the samples were analysed. Every week participants were invited to the clinic when compliance of the ingesting chocolate was verified, blood from these persons was collected, and new batch of one week supply of chocolate was given.

The duration of the trial was 4 weeks. Effects of the following concentrations of lycopene, "L-tug", in the chocolate was studied: 0.0, 0.1, 0.2, 0.3, 0.35, 0.7 mg of lycopene per 1 g of chocolate.

Results
Cholesterol

The effects of chocolate with different concentration of lycopene on the elevated level of the total cholesterol, and other biochemical parameters of the participants are presented in table 4a and table 5.

These results showed that the chocolate with 0.1 mg of lycopene per 1 g of the product was already able to reduce elevated total cholesterol although the changes were not statistically significant. However, chocolate with 0.2 mg of lycopene and above, per 1 g of the product, were consistently producing cholesterol lowering effect in the serum of the participants. The significant effect was already registered from the second week of the trial and reached it maximum by the fourth week.

Biochemistry

The effect of this lycopene/L-tug chocolate on other biochemical parameters was insignificant for the doses studied (table 5). Presumably this was because in most groups these parameters were within their physiological norms and there were no much room for their normalisation/"improvement".

Inflammation and Oxidation

However, the majority of the participants were positive on markers of Inflammatory Oxidative Damage, IOD, or in some cases on presence of such inflammatory markers as LDL-Px and Chl.-IgG. This was probably due that the majority of the participants were between 50 and 60 years old, and these markers can frequently be detected on a subclinical level even in apparently healthy people of this age and above.

It all groups taking L-tug chocolate the reduction of the IOD was significant. However, reduction of two other inflammatory markers was observed only in some groups and was not apparently dose dependent. This inconsistency could be a result of a small number of participants in the tested groups.

Plasma Oxygen Transport

The other interest observation was that ingestion of the L-tug chocolate resulted in the dose-dependent increase of the plasma oxygen transport. This useful property could be used to increase and/or restore supply of the molecular $O_2$ depression or reduction of which may occur not only in many clinical conditions but also during strenuous exercises, or with ageing.

Timing of the Ingestion of Chocolate in Relation to Food Intake.

To evaluate a possible hypothesis that incorporation of lycopene into chylomicrons and lipoproteins, during their re-assembly at the time of digesting food fat, we undertake the following study. We recruited a group of clinically healthy volunteers of similar age and similar level of hypercholesterolaemia.

The design of the study was the same as the study above but instead of taking L-tug chocolate with main food we asked participants to ingest the chocolate between meals—at least two hours after their breakfast, or lunch, and at least two hours before their next meal—lunch or dinner.

The product used was the same format of 10 g containing 0.7 mg of lycopene per 1 g of chocolate.

Results

The results of this study are presented in the table 4b.

It was observed that this regiment was also able to reduce elevated total cholesterol but the significant reduction was only observed on the week 3 of the trial. The maximum of the reduction was on the last $4^{th}$ week.

It was interesting to note, that although the cholesterol-lowering effect was prominent it was still significantly lower that then when the same chocolate was taken during the main meal. If the week 4 is taken as a reference point, the 0.7 mg dose of the L-tug chocolate ingested on the "empty stomach" was more effective that the dose 0.1 but lees effective than dose 0.2 mg when they were taken with food.

TABLE 4a

Dose dependency—chocolate ingestion with main food

| L-tug, per 1 g chocolate | Total serum cholesterol, mg/dL | | | | |
|---|---|---|---|---|---|
| | 0 w | 1 w | 2 w | 3 w | 4 w |
| 0.0 mg | 217 + 4.2 | 215 + 5.6 $\Delta = -2, p^*$ | 215 + 5.1 $\Delta = -2, p^*$ | 214 + 4.9 $\Delta = -3, p^*$ | 213 + 5.3 $\Delta = -4, p^*$ |
| 0.1 mg | 229 + 3.0 | 228 + 6.5 $\Delta = -1, p^*$ | 224 + 3.8 $\Delta = -5, p^*$ | 224 + 2.8 $\Delta = -5, p^*$ | 218 + 1.5 $\Delta = -11, p = 0.01$ |
| 0.2 mg | 228 + 4.1 | 216 + 8.3 $\Delta = -12, p^*$ | 199 + 2.0 $\Delta = -29, p < 0.001$ | 191 + 5.0 $\Delta = -37, p < 0.001$ | 191 + 5.3 $\Delta = -37, p < 0.001$ |
| 0.3 mg | 226 + 6.0 | 202 + 9.3 $\Delta = -24, p^*$ | 198 + 6.8 $\Delta = -28, p < 0.05$ | 196 + 7.3 $\Delta = -30, p < 0.05$ | 192 + 4.3 $\Delta = -34, p = 0.002$ |
| 0.35 mg | 221 + 2.8 | 215 + 3.0 $\Delta = -6, p^*$ | 209 + 2.6 $\Delta = -12, p < 0.05$ | 208 + 2.5 $\Delta = -13, p < 0.05$ | 195 + 8.5 $\Delta = -26, p = 0.02$ |
| 0.7 mg | 241 + 14.0 | 231 + 14.8 $\Delta = -10, p^*$ | 190 + 7.0 $\Delta = -51, < 0.05$ | 188 + 6.3 $\Delta = -53, p = 0.01$ | 186 + 5.3 $\Delta = -55, p < 0.01$ |

TABLE 4b

The chocolate ingestion between meals two hours after and two hours before any food intake

| 0.7 mg | 243 + 13.7 | 230 + 10.1 $\Delta = -13, p^*$ $\Delta_{F[+/-]} = -1$ $p_{F[+/-]} < 0.05$ | 218 + 4.3 $\Delta = -25,$ $p < 0.05$ $\Delta_{F[+/-]} = +28$ $p_{F[+/-]} > 0.01$ | 210 + 5.1 $\Delta = -33,$ $p < 0.05$ $\Delta_{F[+/-]} = +22$ $p_{F[+/-]} > 0.05$ | 208 + 5.8 $\Delta = -35,$ $p < 0.05$ $\Delta_{F[+/-]} = +22$ $p_{F[+/-]} > 0.01$ |

$p_{F[+/-]}$—difference between the same time points in groups which ingested L-tug chocolate with or without food

TABLE 5

Effect of different doses of L-tug Chocolate on biochemical parameters and markers of inflammation and oxidation

| L-tug, per 1 g chocolate | TG mg/dL | HDL mg/dL | LDL mg/dL | glucose | AST | ALT | CRP | IOD in μM | LDL-Px ELISA × $10^2$ | Chl.p-IgG ELISA × $10^2$ | Plasma-$O_2$ |
|---|---|---|---|---|---|---|---|---|---|---|---|
| 0 | 165 ± 12.8 | 40 ± 0.9 | 155 ± 9.9 | 5.9 ± 0.7 | 32 ± 4.1 | 41 ± 5.6 | 5.5 ± 1.4 | 138 ± 11.4 | 354 ± 41 | 675 ± 55 | 0.812 ± 75 |
| | 162 ± 11.5 | 40 ± 0.8 | 154 ± 8.7 | 5.8 ± 0.6 | 34 ± 3.9 | 40 ± 5.1 | 6.1 ± 1.2 | 124 ± 12.7 | 401 ± 38 | 722 ± 64 | 0.823 ± 66 |
| | $\Delta = 3,$ $p > 0.05$ | $p > 0.05$ | $p > 0.05$ | $p > 0.05$ | $p > 0.05$ | $p > 0.05$ | $p > 0.05$ | $p > 0.05$ | $p > 0.05$ | $p > 0.05$ | $\Delta = 11,$ $p > 0.05$ |
| 0.1 mg | 99 ± 3.8 | 43 ± 1.8 | 131 ± 3.8 | 5.4 ± 0.6 | 40 ± 3.8 | 34 ± 3.0 | 6.0 ± 0.9 | 115 ± 10.8 | 175 ± 33 | 577 ± 98 | 1.153 ± 83 |
| | 88 ± 3.3 | 44 ± 1.3 | 127 ± 4.0 | 5.4 ± 0.3 | 36 ± 2.8 | 30 ± 2.7 | 5.4 ± 0.5 | 9 ± 4.6 | 212 ± 59 | 521 ± 67 | 1.263 ± 19 |
| | $\Delta = 11,$ $p > 0.05$ | $p > 0.05$ | $\Delta = 4,$ $p > 0.05$ | $p > 0.05$ | $p > 0.05$ | $p > 0.05$ | $p > 0.05$ | $p < 0.001$ | $p > 0.05$ | $p > 0.05$ | $\Delta = 0.110,$ $p > 0.05$ |
| 0.2 mg | 146 ± 10.3 | 44 ± 0.6 | 145 ± 9.0 | 5.1 ± 0.5 | 29 ± 2.1 | 25 ± 3.0 | 5.1 ± 1.3 | 85 ± 7.8 | 142 ± 19 | 444 ± 22 | 0.811 ± 31 |
| | 120 ± 8.5 | 45 ± 0.5 | 135 ± 8.5 | 6.1 ± 0.4 | 28 ± 1.6 | 25 ± 2.3 | 4.9 ± 1.2 | 19 ± 6.5 | 0 ± 1.8 | 260 ± 18 | 1.363 ± 57 |
| | $\Delta = 26,$ $p < 0.05$ | $p > 0.05$ | $\Delta = 10,$ $p > 0.05$ | $p > 0.05$ | $p > 0.05$ | $p > 0.05$ | $p > 0.05$ | $p < 0.001$ | $p < 0.001$ | $p < 0.001$ | $\Delta = 0.552,$ $p < 0.001$ |

TABLE 5-continued

Effect of different doses of L-tug Chocolate on
biochemical parameters and markers of inflammation and oxidation

| L-tug, per 1 g chocolate | TG mg/dL | HDL mg/dL | LDL mg/dL | glucose | AST | ALT | CRP | IOD in μM | LDL-Px ELISA × 10² | Chl.p-IgG ELISA × 10² | Plasma-O₂ |
|---|---|---|---|---|---|---|---|---|---|---|---|
| 0.3 mg | 162 ± 10.7 | 40 ± 1.0 | 154 ± 3.6 | 4.9 ± 0.4 | 49 ± 8.6 | 60 ± 9.1 | 6.7 ± 1.5 | 155 ± 10.7 | 511 ± 97 | 828 ± 59 | 0.731 ± 37 |
| | 142 ± 9.1 | 41 ± 0.8 | 142 ± 1.8 | 4.7 ± 0.2 | 36 ± 4.7 | 53 ± 10 | 5.5 ± 1.1 | 36 ± 4.1 | 0 ± 38 | 286 ± 49 | 0.963 ± 24 |
| | Δ = 20, p > 0.05 | p > 0.05 | Δ = 10, p < 0.05 | p > 0.05 | p > 0.05 | p > 0.05 | p > 0.05 | p < 0.05 | p < 0.05 | p < 0.05 | Δ = 0.223, p < 0.01 |
| 0.35 mg | 136 ± 28.1 | 43 ± 1.0 | 140 ± 10.0 | 6.3 ± 0.4 | 41 ± 2.4 | 49 ± 4.0 | 6.4 ± 1.7 | 130 ± 20.8 | 160 ± 36 | 552 ± 41 | 0.988 ± 24 |
| | 106 ± 16.5 | 44 ± 1.5 | 132 ± 9.3 | 5.5 ± 0.3 | 39 ± 2.3 | 45 ± 4.1 | 5.8 ± 1.6 | 55 ± 8.8 | 206 ± 47 | 506 ± 66 | 1.263 ± 19 |
| | Δ = 30, p > 0.05 | p > 0.05 | Δ = 8, p > 0.05 | p > 0.05 | p > 0.05 | p > 0.05 | p > 0.05 | p < 0.05 | p > 0.05 | p > 0.05 | Δ = 0.275, p < 0.001 |
| 0.7 mg | 128 ± 10.8 | 42 ± 0.6 | 153 ± 3.8 | 5.4 ± 0.2 | 29 ± 2.5 | 29 ± 3.5 | 6.8 ± 0.8 | 86 ± 9.9 | 66 ± 12 | negative | 1.099 ± 87 |
| | 105 ± 6.6 | 43 ± 0.7 | 141 ± 3.0 | 6.0 ± 0.4 | 29 ± 2.0 | 27 ± 1.8 | 6.6 ± 0.5 | 25 ± 7.8 | 3 ± 8.5 | negative | 1.430 ± 85 |
| | Δ = 20, p > 0.05 | p > 0.05 | Δ = 8, p > 0.05 | p > 0.05 | p > 0.05 | p > 0.05 | p > 0.05 | p < 0.05 | p < 0.05 | | Δ = 0.331, p < 0.01 |

Postprandial Study 8 clinically healthy volunteers 4 males and 4 females, age 35-60 years old, were recruited for this study.

Main inclusion criteria were:
- all patients were naive, for at least 3 months prior to the study, for any lipid-lowering medications, dietary supplements or special lipid or weight management diets,
- willing participate in the study.

All volunteers received standardise fat rich meal comprising of 50 g of butter as a part of a sandwich with 2 slices of white bread. Then without any break volunteers were asked to ingestion 10 g chocolate bar without lycopene. During intake of this test meal volunteers was given 200 ml of warm decaffeinated tea with skimmed milk containing no more than 1% of dairy fat.

The blood was collected just before the intake of the meal and every hour for 4 hours after that.

After one week of break the same volunteers were ask to take exactly the same meal of 50 g of the same butter with two slices of the same white bread. Then each of them was asked to take 10 g of the chocolate bar with 7 mg of lycopene blended in at the protocol described above. The same type and the volume of tea was allowed, and the blood was collected at the same protocol as in the previous week.

The results of this cross-over study are presented in the table 6. They show that ingestion of lycopene-contained chocolate was able to reduce elevation of postprandial triglycerides about two fold and cholesterol between 2 and 3 times. I was also interesting to note that the postprandial glycaemia was also reduced by this L-tug chocolate.

The most remarkable changes were observed when this chocolate with the embedded lycopene was not only able to prevent increase of the inflammatory oxidative markers in the postprandial blood but even cause their reduction below the baseline level (table 6).

TABLE 6

Statistically significant between control and L-tug trials
Effect of L-tug chocolate on Postprandial Biochemistry Profile and Markers of Inflammatory Oxidation
in Serum of Healthy Volunteers—Cross-over Study

| Postprandial time | Trial A (control) 50 g butter − 10 g chocolate (n = 0) | | | | | Trial B 50 g butter + 10 g L-tug chocolate (n = 6) | | | | |
|---|---|---|---|---|---|---|---|---|---|---|
| | TC in mg/dL | TG in mg/dL | LDL in mg/dL | Glucose in mmol/L | IOD, μM MDA | TC in mg/dL | TG in mg/dL | LDL in mg/dL | Glucose in mmol/L | IOD, μM MDA |
| baseline | 184 | 108 | 153 | 5.0 | 87 | 180 | 109 | 135 | 5.0 | 86 |
| 1 h | 208 | 119 | 136 | 6.0 | 94 | 206 | 174 | 136 | 5.9 | 87 |
| | Δ = 24 ± 5.7 | Δ = 11 ± 3.9 | Δ = 3 ± 0.2 | Δ = 1.0 ± 0.5 | Δ = 7 ± 0.7 | Δ = 18 ± 4.6 $p_{(A-B)} > 0.05$ | Δ = 15 ± 2.9 $p_{(A-B)} > 0.05$ | Δ = 3 ± 0.2 $p_{(A-B)} > 0.05$ | Δ = 0.9 ± 0.2 $p_{(A-B)} > 0.05$ | Δ = 1 ± 0.5 $p_{(A-B)} > 0.05$ |
| 2 h | 215 | 129 | 136 | 6.1 | 97 | 202 | 120 | 135 | 5.7 | 49 |
| | Δ = 31 ± 5.2 | Δ = 21 ± 5.3 | Δ = 3 ± 0.2 | Δ = 1.1 ± 0.1 | Δ = 10 ± 0.6 | Δ = 14 ± 4.7 $p_{(A-B)} < 0.01$ | Δ = 11 ± 2.6 $p_{(A-B)} < 0.05$ | Δ = 2 ± 0.1 $p_{(A-B)} > 0.05$ | Δ = 0.7 ± 0.1 $p_{(A-B)} < 0.05$ | Δ = 3 ± 0.6 $p_{(A-B)} > 0.05$ |
| 3 h | 204 | 120 | 135 | 5.6 | 97 | 194 | 114 | 135 | 5.4 | 72 |
| | Δ = 20 ± 5.3 | Δ = 12 ± 3.1 | Δ = 2 ± 0.1 | Δ = 0.6 ± 0.2 | Δ = 10 ± 0.9 | Δ = 6 ± 4.5 $p_{(A-B)} < 0.05$ | Δ = 5 ± 2.4 $p_{(A-B)} < 0.05$ | Δ = 0 ± 0.1 $p_{(A-B)} < 0.05$ | Δ = 0.4 ± 0.1 $p_{(A-B)} > 0.05$ | Δ = 14 ± 1.3 $p_{(A-B)} < 0.01$ |
| 4 h | 193 | 110 | 131 | 5.3 | 99 | 195 | 110 | 133 | 5.1 | 70 |
| | Δ = 9 ± 4.4 | Δ = 2 ± 3.4 | Δ = 1 ± 0.2 | Δ = 0.3 ± 0.2 | Δ = 12 ± 1.3 | Δ = 7 ± 4.2 $p_{(A-B)} > 0.05$ | Δ = 1 ± 2.7 $p_{(A-B)} > 0.05$ | Δ = 0 ± 0.2 $p_{(A-B)} > 0.05$ | Δ = 0.1 ± 0.2 $p_{(A-B)} > 0.05$ | Δ = 16 ± 1.1 $p_{(A-B)} < 0.01$ |

TC—total cholesterol, TG—triglycerides, Δ—changes in mean concentrations with the baseline, $p_{(A-B)}$—statistical differences in same parameters at the same time points between trial A and trial B.
8 clinically healthy volunteers, 4 men and 4 women, average age—35-60 years old New Opportunities to Control Lipid Metabolism Inflammation and Tissue Oxygenation The results presented here open a possible new mechanisms and new ways not only to control already developed changes in the lipid metabolism but also to prevent these changes.

These results also provide for the development of new ways to control subclinical and other forms of inflammation and/or boosting transport of the plasma molecular oxygen, which could be useful to restore tissue oxygen saturation which could be important in many clinical conditions and to delay ageing.

The results described herein are unexpected because the benefit of adding any ingredient with additional health value to a chocolate product would be expected to be outweighed by the potential harmful consequences of consuming increased amounts of this high-fat food product.

Reducing fat content in food products is the standard way to minimise their fat load to the body. However this approach is not generally useful for cocoa-based products, such as chocolate, because fat reduction negatively affects the melting, feeling and taste properties.

The results described herein show the unusual and unexpected outcome of the blending of carotenoids such as lycopene with cocoa-based products. Not only is cocoa butter prevented from contributing to the rise of blood lipids, but the blend actively reduces lipids which are already at an elevated level.

In other words, the invention described herein not only makes cocoa products, such as chocolate, "safer" from the health impact point of view, but may also make it useful as a proactive interventional product for slimming, lipid-lowering purposes and anti-aging purposes, and for prevention and help in management of metabolic, pre-diabetes, cardiovascular and other conditions.

The invention claimed is:

1. A method of:
    reducing levels of cholesterol, LDL and triglyceride in the blood of an individual, the method comprising administering chocolate comprising a carotenoid compound to said individual;
    wherein the chocolate comprises between 0.1 to 1 mg of the carotenoid compound per one gram of chocolate; and
    wherein the carotenoid compound is selected from the group consisting of lutein, lycopene, astaxanthin, and b-carotene; and
    wherein levels of cholesterol, LDL and triglyceride are reduced compared to the level in the said individual before administration of said chocolate.

2. The method of claim 1, wherein:
    (a) said individual has Metabolic Syndrome, obesity, type II diabetes or atherosclerosis and clinical complications thereof; or
    (b) the food product is consumed during a mealtime.

3. The method of claim 1, wherein the carotenoid compound is lycopene.

4. The method of claim 1, wherein the individual has elevated blood levels of cholesterol, wherein the level of cholesterol is more than 200 mg/dL.

5. The method of claim 1, wherein the individual has elevated levels of triglycerides, wherein the level of triglyceride is more than 150 mg/dL.

6. The method of claim 1, wherein the chocolate comprises 0.2 mg/g of the carotenoid compound.

* * * * *